United States Patent
Blattner et al.

(10) Patent No.: US 6,739,108 B2
(45) Date of Patent: May 25, 2004

(54) FRAGILE CONTAINER HANDLING SYSTEM FOR RETORT/STERILIZATION PROCESSES

(75) Inventors: Michael F. Blattner, Covington, LA (US); Christopher G. Greve, Covington, LA (US)

(73) Assignee: Allpax Products, Inc., Covington, LA (US)

( * ) Notice: Subject to any disclaimer, the term of this patent is extended or adjusted under 35 U.S.C. 154(b) by 0 days.

(21) Appl. No.: 10/261,421

(22) Filed: Sep. 30, 2002

(65) Prior Publication Data

US 2004/0060263 A1 Apr. 1, 2004

(51) Int. Cl.$^7$ ................................................ B65B 35/30
(52) U.S. Cl. ............................ 53/247; 53/543; 53/539; 53/250; 53/252; 53/448
(58) Field of Search .......................... 53/443, 447–448, 53/153, 534–535, 169, 543, 539, 250, 252, 247

(56) References Cited

U.S. PATENT DOCUMENTS

| | | | | |
|---|---|---|---|---|
| 3,805,476 A | * | 4/1974 | Kawamura et al. ........... | 53/448 |
| 5,070,992 A | * | 12/1991 | Bonkowski .................... | 53/543 |
| 5,197,261 A | * | 3/1993 | Hartness et al. .............. | 53/534 |
| 5,546,734 A | * | 8/1996 | Moncrief et al. ............. | 53/543 |
| 6,098,379 A | * | 8/2000 | Spatafora et al. ............ | 53/448 |

* cited by examiner

*Primary Examiner*—Rinaldi I. Rada
*Assistant Examiner*—Michelle López
(74) *Attorney, Agent, or Firm*—Joseph T. Regard Ltd (57) ABSTRACT

A system for loading retorts, sterilization systems, and the like. The preferred embodiment of the present system provides both loading and unloading modules, the loading module designed to automatically load fragile containers, in mass and layer by layer into a self-supporting cube array of stacked trays nested in a basket frame. The unloader module automatically unloads the cube array layer by layer after the contents of the cube array are processed in mass. The stack of trays, or batch cube remain as an intact, stacked unit throughout the entire retort process. A hydraulic ram which is associated with each the loader and unloader, lifting the batch cube from the basket frame and indexing the batch cube vertically during the loading/unloading process, respectfully. Each layer in the stack is either loaded or unloaded as that layer is positioned in the home position. Both the loader and unloader includes home position locating devices or tray supports that accurately position the batch cube so that product can be transferred onto or off of the conveyor. In the loader module, a multi-position container break is used to collate each layer prior to transfer into the batch cube system. There are a total of three break locations. A clearing assembly is provided to assure that no containers are left on the dead plate. Also taught is a tip indicator which detects when a container has been knocked over or otherwise improperly oriented during the loading process.

30 Claims, 6 Drawing Sheets

FRAGILE CONTAINER HANDLING SYSTEM FOR RETORT/STERILIZATION PROCESSES

FIELD OF THE INVENTION

The present invention relates to loaders, and particular to a system for loading retorts, sterilization systems, and the like. The preferred embodiment of the present system provides both loading and unloading modules, the loading module designed to automatically load fragile containers, in mass and by layer into a unique self-supporting cube array of stacked trays (hereinafter referred to as batch cube which remain intact and are conveyed to and from the unloaders by a basket frame. The unloader module automatically unloads the containers after the cube array and its contents have been processed, in layer-by-layer fashion.

The batch cube remains intact as a stacked unit throughout the entire retort process, transported and enveloped by a basket frame. A hydraulic ram which is associated with each the loader and unloader, indexing the batch cube vertically during the loading/unloading process. Each layer in the stack of trays forming the batch cube is either loaded or unloaded as that layer is positioned in the home position. Both the loader and unloader includes home position locating devices or tray supports that accurately position the tray or cube array out of the basket frame and to the appropriate position so that product can be transferred onto or off of the conveyor.

In the loader module, a multi-position container break is used to collate product prior to transfer into the tray system. There are a total of three break locations. A clearing assembly is provided to assure that no containers are left on the dead plate.

Lastly, a tip indicator is taught wherein the unit is able to detect when containers which have been knocked over or are otherwise improperly oriented with regard to the cube array during the loading thereof.

BACKGROUND OF THE INVENTION

Most shelf stable products have historically been processed in metal cans or glass containers, which are typically processed in a mass in a retort basket or the like. These containers are very rigid and not prone to damage when using conventional retort basket loading techniques. These containers are rigid enough that each layer can be stacked in the basket upon the previous layer with no damage to the containers in the lower quadrant of the stack. Perforated layer pads or divider sheets are typically placed between each layer to separate same.

Because of consumer preferences and lesser costs, flexible and fragile containers have begun to be used in increasing numbers. This trend started in the mid 1980 s and has increased significantly starting in the late 1990 s. As the consumer demand for this type of packaging increases, food processors have been faced with the difficult chore of handling these containers at higher and higher line speeds.

Unlike a rigid container like a metal can or glass bottle, these containers cannot support the weight of additional containers being loaded one layer on top the next. Examples of fragile containers include plastic bottles, trays, cans, cups, and bowls, and various laminated packaging. The geometry of these packages can include cylindrical, rectangular, and various other irregular shaped containers. Since most production lines require elevated line speeds to be commercially feasible, the best method to transfer or load these types of containers is to do so in mass. However, the prior art fails to provide such a system.

Existing loading devices that have been used to handle flexible pouches and some fragile containers use a pick and place methodology, which may or may not allow for a full layer of containers to be handled at one time. In addition to handling the container, this type of handling approach also requires secondary handling of the trays. Each layer must be staged for loading or unloading and then collated into a formed stack. There is also additional handling, which must be done to manage the flow of racks between the unloader and loader. All of this secondary handling makes the equipment design more complex, more costly, and in many cases limits the operational speed of the line.

SUMMARY OF THE INVENTION

Unlike the prior art, the present invention seeks to provide a system for the loading and unloading of fragile containers which cannot be stacked upon one another which is reliable and fast in operation, and relatively cost effective to operate and maintain.

In this regard, the present invention provides a system for loading and unloading fragile containers for the retort or sterilization process in a manner that will eliminate the damaging vertical, downward forces that cause container deformation and do so at commercially accepted line speeds. The invention eliminates the unnecessary complexities and costs seen with secondary tray handling currently being utilized.

The present invention provides an apparatus suitable for handling multiple containers types including: plastic bottles, plastic cans, plastic cups, and various laminated packaging. The geometry of these packages can include cylindrical, rectangular, and various other irregular shaped containers. The containers can be handled either in lanes or in a nested pattern. The invention is applicable for any type of horizontal retort which uses square or rectangular baskets.

The methodology used in this invention is to handle the transfer one full layer at a time in a specialized, one piece, multi-layer transport and processing cube array. While the array is referred to as being a cube shape, this is not meant to be limiting, as the array can comprise any rectilinear or other configuration, depending upon the application. The number of containers to be treated in a layer is a function of the size of the container being loaded and the size of the cube or basket that will fit inside the retort or sterilizer. The methodology used in the invention allows the stack of trays that forms the batch cube to always stay together.

Thus, the need for secondary handling (i.e., stacking the goods to be treated upon one another in a layering manner) is completely eliminated. The batch cube can either be contained within a basket or basket frame, as illustrated in the preferred embodiment of the present invention. As will be shown, the trays can include lanes which allow the product to be staged by lanes or can have an open configuration which allows for a nested pattern of containers.

In either case, the cube of trays is indexed up and down and stops at the home position so that the layer of containers can be transferred. Each layer in the cube will visit the home position until the entire cube is emptied or filled. The side loading of the trays cube is what allows the cube to stay together as a unit and eliminates the need to stack and de-stack the cube like what is done with pick and place systems.

The invention includes both a loading module and unloading module. Both modules are almost identical with the exception of the direction of operation and a few components like the break feature. This fact aids in the economy of both the fabrication and the ongoing operation of the modules. Both modules are controlled by an independent PC or PLC. The PC or PLC controls allow for fully automatic operation of the machines.

Both the loader and unloader module include an independent, servomotor driven, linear motion mechanism used to push the containers into or out of the tray a Pusher. Another independent, servomotor driven, linear motion mechanism is used as a follower to assure that containers are not tipped during the transfer process a Follower. This feature is required if the modules are to be operated without the presence of a human operator. Both the Pusher and Follower are equipped with a breakaway mechanism that will trip in the event that a container is tipped over. Both breakaway mechanisms are equipped with a detection switch that sends a tipped container signal to the PLC or PC controlling the modules.

Both the loader and unloader module can include components for determining the accurate location of the tray cube, including proximity switches, photosensors, or other tracking means. The hydraulic ram mechanism is used to provide coarse positioning of the cube within the module, lifting the cube from the basket frame so that the tray to be loaded is in the appropriate position. A tray support mechanism is used for final and accurate positioning of the layer being loaded or unloaded. This part of the mechanism is essential to assure a final, accurate location prior to container transfer. The mechanism eliminates cumulative dimensional error within the cube and provides needed support for trays and basket frame so that deflection error is also eliminated.

A multi-position can brake is used in the loader module to allow proper staging of each layer of containers into the tray to be loaded. Unlike conventional brakes (which may use, for example, pick and place loading techniques), the present invention utilizes linear, horizontal motion to convey the product into the trays, which eliminates the damaging effects of a top pressure brake used for metal cans or other rigid containers.

A conveyor is used to transport the cubes to and from each module. This conveyor is oriented transverse to each module and straddles the hydraulic push mechanism. The push plate actuates up and down through the conveyor frame and allows the cube to be moved for positioning at the load or unload position.

The above components working together form a new and innovative loading/unloading system which is not contemplated or otherwise suggested by the prior art.

It is therefore an object of the present invention to provide a loading/unloading system for retorts or sterilizers which can accommodate the new generation of polymer, laminated, or other containers which cannot be stacked upon one another.

It is another object of the present invention to provide a loading/unloading module which automatically loads fragile containers to a multi-shelf, multi-channel cube of trays in a basket frame.

It is another object of the present invention to provide a tip mechanism which indicates if an object being loaded is improperly oriented.

It is another object of the present invention to provide a loader/unloader system which fully automates the process and limits secondary handling of the trays, and wherein the nested trays or batch cube remains intact through the treatment process.

Lastly, it is still another object of the present invention to provide a loader/unloader for fragile containers which is cost effective to implement and maintain, reliable in operation, while providing a speed and operational performance on par with loaders for rigid goods.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DESCRIPTION OF PREFERRED EMBODIMENT

The preferred embodiment of the present invention contemplates a batch loader and unloader for simultaneously processing a number of fragile containers through a retort, sterilization apparatus, or similar system.

Figure 5:
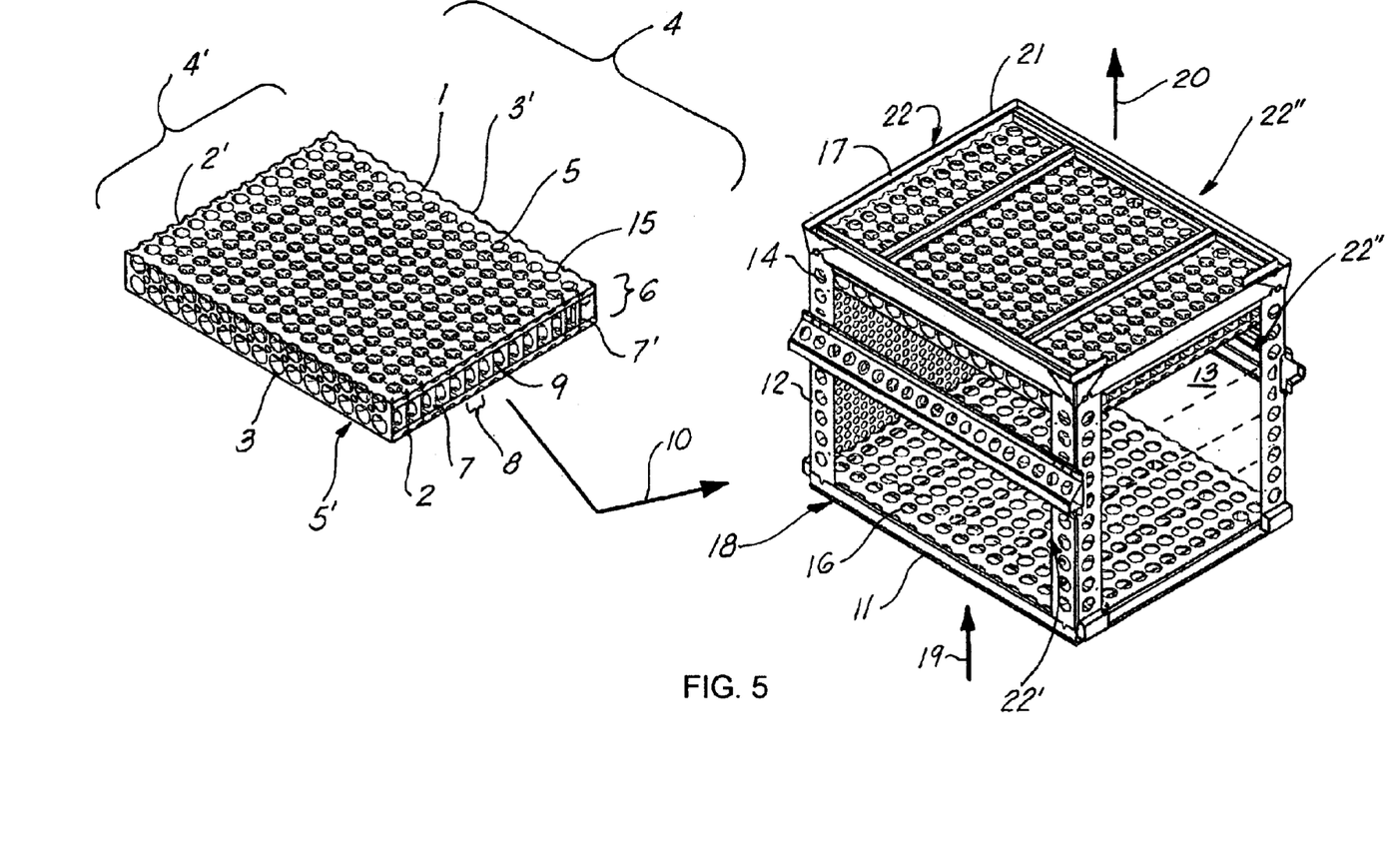
FIG. 5 is a close-up, isometric view illustrating in detail the individual tray and basket frame forming batch-processing basket utilized with the invention of FIG. 1.

Referring to FIG. 5 of the drawings, a batch-processing basket 14 in the form of a frame having a plurality of trays vertically situated therein in is utilized in the loading and conveying of the product for processing in the retort, sterilizer, or other process. As shown, a batch cube is securely held within the basket frame 11, allowing the batch processing basket, once the trays have been loaded and positioned therein, to be oriented 360 degrees and remain intact.

Each tray 1 has first 2 and second 2' ends, first 3 and second 3' sides, a length 4, a width 4', and top 5 and bottom 5' walls forming an enclosure 16 having a height 6 therein. The enclosure is divided equally via parallel vertical divider walls 7, 7', forming individual cells 9, 9" or linear compartments, each having sufficient width 8 and height 6 for receiving a row or line of product along the length 4 of the tray. In the preferred embodiment, the trays are formed of stainless steel with apertures 15, 15' for providing uniform heat distribution and transfer to product situated therein.

Multiple trays are stacked 10 upon and affixed to one another forming a batch cube 13, which is selectively enveloped by a basket frame 11 which includes a structure 12 to encapsulate the openings of the trays, as well as securing the trays in stacked configuration at any orientation, the trays together forming the batch processing basket 14. In the example shown, six trays are stacked and secured to one another for placement into the basket frame to form the batch cube.

The basket frame has an open top 17 and bottom 18, and which may include an H Frame 21 for distributing clamping force during the retort process, for use in a rotary retort. The floor 16 of a bottom tray situated in the base of the basket frame, is shown in a cut-away view. In loading or unloading the batch cube 13, upward pressure 19 is provided to the floor 16 of the bottom tray while the basket frame is held stationary, so as to urge the batch cube 13 forming the stack of trays up 20 and out of the basket frame 11, where the open ends 2, 2' of the trays and compartments 9 are positioned so as to be accessible for loading or unloading product therein, as will be further discussed infra.

It is noted that the side walls 22, 22', 22", 22' of the basket frame 11 may be clad with stainless sheeting having apertures therein similar to the walls forming the trays, for structural reinforcement and to keep product loaded in the trays from falling out during processing.

Loader Module

Referring to FIGS. 1, 1A, 4 and 5, a loader module 30 is provided having first 31 and second 32 ends, a flat upper work surface 33 having a generally rectilinear configuration having raised edges 42 at least partially thereabout, and a loader conveyor system 46 for conveying product from the first end 31 of the loader to the tray 39 to the actual loading area. The upper work surface 33 is supported in spaced relationship above the floor via legs 34.

Figure 1:
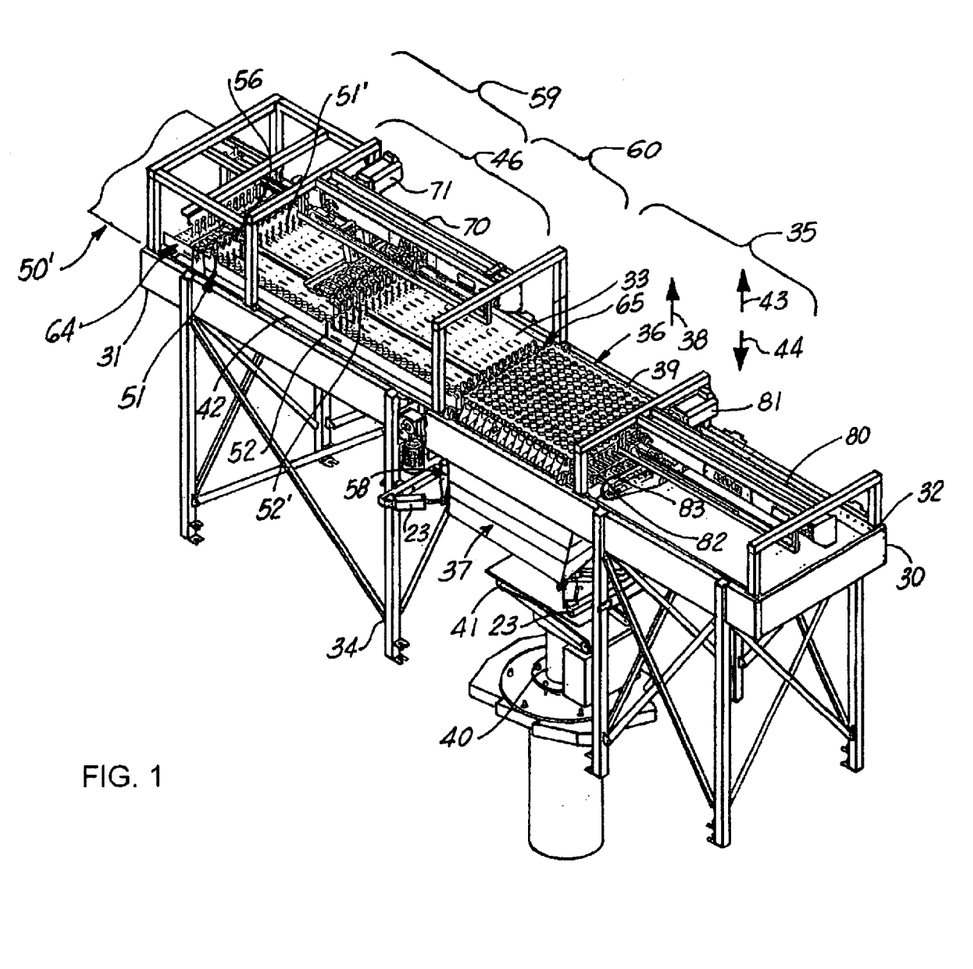
FIG. 1 is a side, isometric view of the loader of the preferred embodiment of the present invention.
Figure 1A:
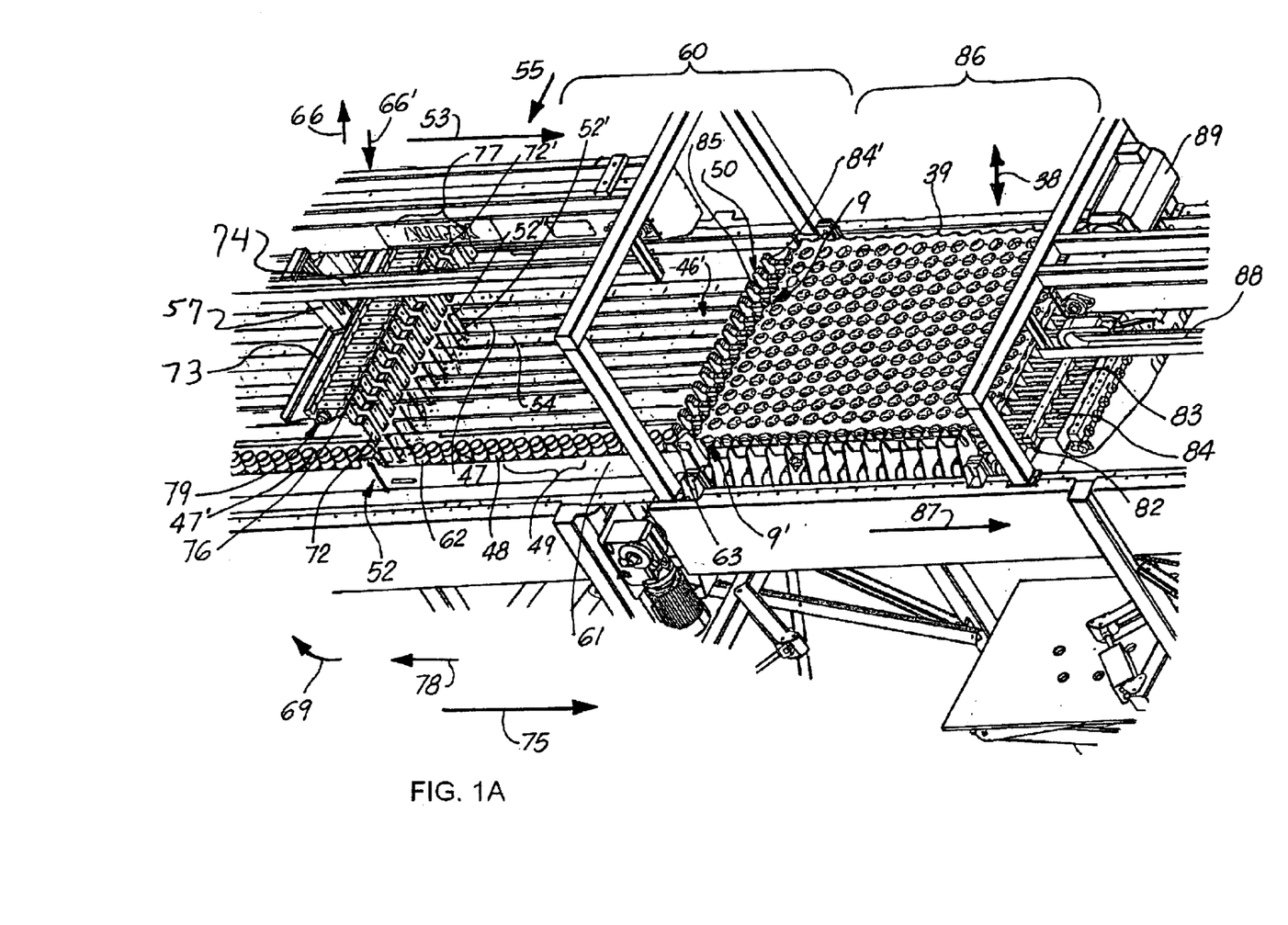
FIG. 1A is a partial, close-up, isometric view of the loader of FIG. 1, illustrating the tray positioner section, pusher section, brakes, and follower section of the device.

An opening 36 is formed through the medial portion 35 of the work surface 33 in the loader module for allowing the passage of the batch cube, so that a layer formed by one tray 39 can be indexed for loading, the tray emanating from the basket frame 37 hereunder, each of the trays in the stack of trays in the batch processing basket configured to be vertically indexed 38 through opening 36 via computer control, so that the product receiving compartments 9 for each tray may be positioned at work surface 33 level via a computer controlled lift mechanism 41.

The lift mechanism 41 may be operated by, for example, a hydraulic ram/push plate 40, servo motor, or the like, and is configured to raise 43 or lower 44, the batch cube to facilitate the loading of product into each tray forming the batch processing basket 37. The hydraulic ram/push plate 40 provides coarse positioning of the batch cube within the loading module. A tray support mechanism 23 locks to the batch cube and is powered by pneumatic cylinder 58, providing a more accurate, final positioning prior to container transfer for each tray to be loaded, to eliminate cumulative dimensional errors while providing support to prevent deflection errors in the system.

The hydraulic ram/push plate is comprised of a hydraulic cylinder which is attached to a flat, push plate and to an anti-swivel linkage. The cylinder is encased in a flanged casing which is sunk into a hole placed in the floor and secured to the floor by means of top mounted flange. The push plate and controls are located above floor level.

The first end 31 of the loader module 30 receives product from an external conveyor 50', wherein the product passes over a dead plate and on to the loader conveyor system 46 of the loader module. In the preferred embodiment of the present invention, the loader conveyor system 46 comprises a series of evenly spaced mini conveyor belts 46', each belt having width to accommodate the width of a single line of the product to be conveyed, each belt separated by divider wall 47' to maintain product 48 traveling along a belt in along a centered, single line 49 on each said belt, each belt configured to end 50 adjacent to the opening of each compartment 9 in the tray to be loaded 39, thereby conveying 53 product to the opening of the compartment to be loaded.

In the present example, the exemplary tray 38 has fourteen compartments 9 for receiving a row of product; accordingly, there is provided fourteen mini conveyors belts 46', situated in aligned fashion along the length of the conveyor area 46 from the first end 31 of the loader unit to the vicinity of the opening of the commensurate aligned compartment 9 in the tray in position to be loaded, which tray is a level in a batch cube in a basket frame which has been conveyed to the loader via conveyor and positioned and indexed via lift 41.

For consistency of processing, it is important that each product to be treated is uniformly oriented, and each compartment of each tray has an equal number of product situated therein, so as to provide maximum efficiency and uniform heat transfer in the retort or sterilization process. Accordingly, the present invention includes means to monitor proper orientation, collation, spacing and number of items loaded.

With this in mind, the loader of the present invention includes first 51, second 52 and third 65 computer controlled brake systems, each brake system comprising a line of transversely situated, individually computer controlled barriers in the form of vertically oriented rods 52' having first and second positions, wherein in the first position each rod 52' is situated in an open state adjacent to a divider wall as shown, and a second position 52" whereby the rod is moved sideways 55 to a position medial to the conveyor path and between first and second divider walls about the conveyor path, so as to temporarily block further passage of product therethorough, thereby selectively regulating the feeding of product along the conveyor lines.

These break systems may work in cooperation with proximity detectors, which may be set to have the barriers (vertically oriented rods) moved from an open to closed position when it is detected that the mini conveyor belt beyond the barrier has full capacity product, or alternatively on a timing cycle, so as to facilitate loading of the desired number of product into the compartments 9 formed in the trays for receiving same. Further, other means of selectively preventing the continued passage of product along a conveyor may likewise be implemented, including without limitation, raised or lowered barriers, etc.

The barriers, which may be controlled via individual actuators or servos, are configured to provide uniform placement of product into a final loading area 60. For example, 14 individual conveyor lines are shown in loading area 60, conveyor line one 61 being the first line, having shown therein exemplary polymer bottles containing food therein for retort processing. As shown, conveyor line one 61 has a capacity of handling eighteen bottles, which is the predetermined amount of bottles which can be held in an upright position by the first compartment 9' in tray 39.

It is further noted that the system of the present invention may utilize other means of directing product to the loading area, including a single large conveyor belt with or without divider walls, depending upon the nature of the product being loaded, and the presently taught mini-conveyor belt/divider wall embodiment is provided for illustrative purposes only and is not intended to be limiting as to the scope of claims of the present invention.

Returning to the drawings, in the preferred embodiment of the present invention, product from external conveyor 50' passes over a dead plate, through first brake 51 (which is in an open position), where the product is urged upon the plurality of adjacent mini conveyors comprising the loader conveyor system 46.

The product advances down the loader conveyor system 46 until it reaches the second brake 52, which is in a closed position 52". Once the product or containers form a full layer behind second brake 52 (detected by full layer detector 56, which comprises, for example, a line of proximity switches, light sensor, weight sensor, etc), second brake 52 is opened, so that the containers in the preliminary loading area 60 are allowed to advance to the final loading area 59; third brake 65 is closed to "park" the multiple lines of product to be loaded into the tray at their respective openings of the compartments in the tray to be loaded.

Thus, in the present example, once all fourteen mini conveyor belts 54 situated in the preliminary loading area 59 are stocked with the determined amount of product (in this exemplary case, eighteen bottles each), which comprises the exact amount of product to fill each compartment in the tray 39 to be loaded, thereby providing fourteen lines product to be loaded in the final loading area, each line having first 62 and second 63 ends.

Situated over the final loading area 60 is a pusher 70 for urging the product situated along the fourteen lines into respectively aligned and positioned fourteen compartments in the positioned empty tray 39, While a follower 80 is provided to engage the second end 63 of each line of product for loading, the follower configured to support the each line of product in an upright position while the pusher urges same into each compartment 9 of the tray 39. Upon initiation of the pusher 70 and follower 80, the third brake 65 is opened to allow the product in the final loading area to be urged therein, as discussed below.

As shown, the pusher 70 and follower 80 are linear motion mechanisms each utilizing their own servo motors 71, 81 to push and support the product 48 ready for loading in the final loading area into the tray positioned for loading. The pusher comprises a plurality of aligned pusher paddles 72, 72' situated in equidistant spacing on carriage 73, each paddle aligned above a respective mini conveyor 54 in the final loading area 60, so as to push 75 a line of product situated upon said mini conveyor into an aligned compartment in the empty tray 39, positioned for loading.

The carriage 73 is transversally supported by pneumatic cylinder 57 which can raise 66 or lower 66' the carriage and pusher paddles to allow the passage of product thereunder when the pusher is not in use, the vertical servo affixed to a linear track 74, which in turn guides the carriage and pusher paddles below said linear track 74 by the servo motor 71, and is computer controlled. As indicated, the carriage has situated along its length a pusher paddle 72 above each mini conveyor in the loading area, each pusher paddle configured to engage the first end 62 of the product to be urged 75 along the final loading area 60 and loaded into their respectively aligned compartment 9' in the tray 39 to be loaded.

The follower 70 works in conjunction with the pusher, and likewise includes a carriage 82, but instead of pusher paddles, the carriage 82 has situated thereon a number of follower arms 83 commensurate with the number of compartments 9' in the tray to be loaded (in this case, 14), the follower arms 83 having first 84 and second 84' ends, the first 84 ends engaged and supported by the carriage 82, the second ends 84' having an engagement end 85 for engaging the second end 63 of the row of product to be loaded to prevent same from tipping, each follower arm 83 further having a uniform length 86 to allow passage of a single engagement end completely through each respective compartment 9' in the tray to be loaded.

Like the pusher 70, the carriage 82 of the follower 80 is guided along a linear track 88 by a servo motor 89 so as to allow the engagement end 85 of each follow arm 83 to engage and support the second end of the row of product to be loaded while the pusher 70 is pushing or urging 75 the first end of the product to be loaded into the compartments of the empty tray 9 positioned for loading. During this operation, the follower 80 is retracting 87 the follower arms 83 at about the same speed that the pusher 70 is pushing or urging 75, while maintaining the engagement end 85 of the follower arms against the product being loaded into the tray 39.

Further provided in the present invention is a tip detector mechanism 77 for detecting when a container has tipped over from its upright position during loading into the tray. In accomplishing this feature, each pusher paddle 72 is pivotally affixed 76 to the carriage 73, but held in a vertical position via a trip mechanism to a predetermined level of resistance 78. If the pusher paddle is pushing a row of product into a tray and one of the product containers is tipped over, it provides resistance against said pusher paddle to further forward movement through the pusher s predetermined cycle, exceeding the trip force, causing the trip mechanism to release the pusher paddle, causing the pusher paddle to pivot, which pivot is detected by a light beam// sensor or mechanical switch, which alerts the operator of the tipped product and halts loading until the problem is corrected. Upon the operator reorienting the tip product and resetting the pusher paddle by re-orienting it vertically, the loader may be reactivated to complete the loading operation.

Likewise, the each follower arm is designed with a breakaway point which like the pusher, will trip in the event of a tipped container. In the even of a tripped arm, the follower trip switch or light beam/sensor will be interrupted to detect the tripped lane.

The pusher and follower are sequenced to move simultaneously, the pusher urging 75 the product into the tray, while the follower, contacting the product at the second end of the line, retracting 87 as the product is loaded into the tray. Once the product is fully loaded, the follower is fully retracted so that no portion of the follower arms is present in the tray, so that the batch cube in the basket frame 37 may be vertically sequenced 38 to position the next empty tray into position for loading, until the processing basket 37 is full.

Once the product containers are fully inside tray, the tray batch cube is vertically indexed 43 one position via lift mechanism 41, and the next tray is staged for loading. The product is collated to the final loading area mini conveyor belts as discussed above, forming in this case fourteen lines of product, the pusher/follower urges the product into the tray compartments, the next tray is indexed into position, and the procedure is repeated until the entire batch cube of trays is loaded.

Again, the number of trays in a batch cube, and the number of compartments in each tray is dependent on both the size of the stack and the dimensions of the product containers to be processed, although the exemplary batch-processing basket of the present example is shown as a six-tray stack. Once the entire stack of trays forming the batch cube has been loaded, it is indexed away 24 from the loader module by means of the transverse mounted conveyor 104' adjacent to the lift mechanism. The next basket frame and batch cube forming the batch processing basket is then loaded from the transverse conveyor 104' and indexed into position.

Figure 2:
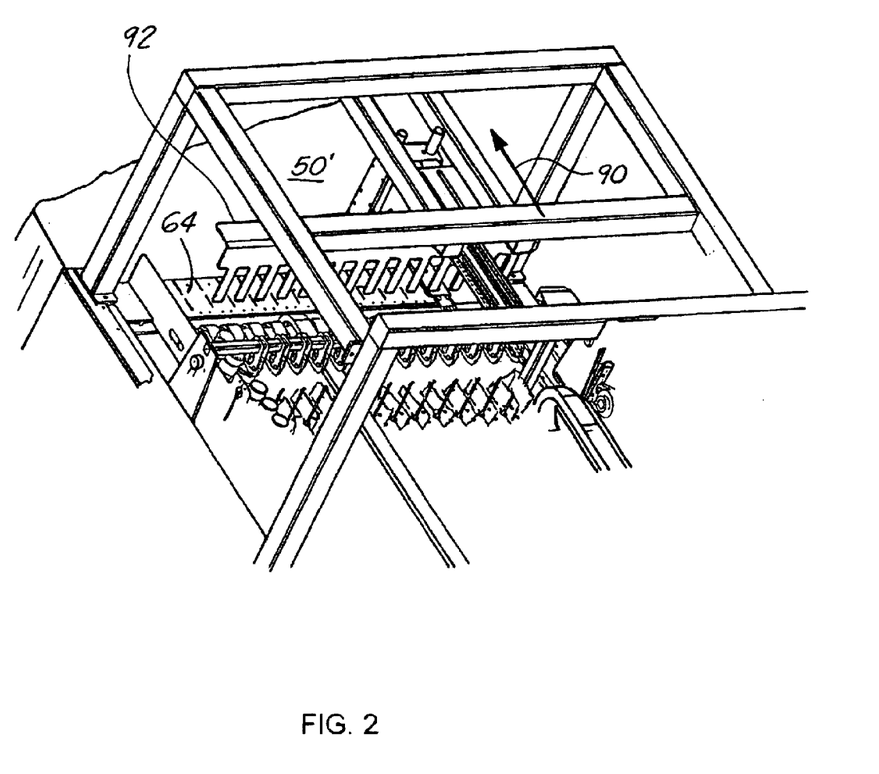
FIG. 2 is a close up, isometric view of the invention of FIG. 1, illustrating in detail the clearing assembly section of the system.

Referring to FIG. 2, a clearing assembly 92 comprising a carriage transversally situated above the dead plate 64, providing an independent, servomotor driven, linear motion mechanism to clear 90 product remaining on the dead plate after the loading cycle has been completed, conveying the product back to the external conveyor 50', to prevent accumulation and blockage of loader.

Unloader Module

Figure 3:
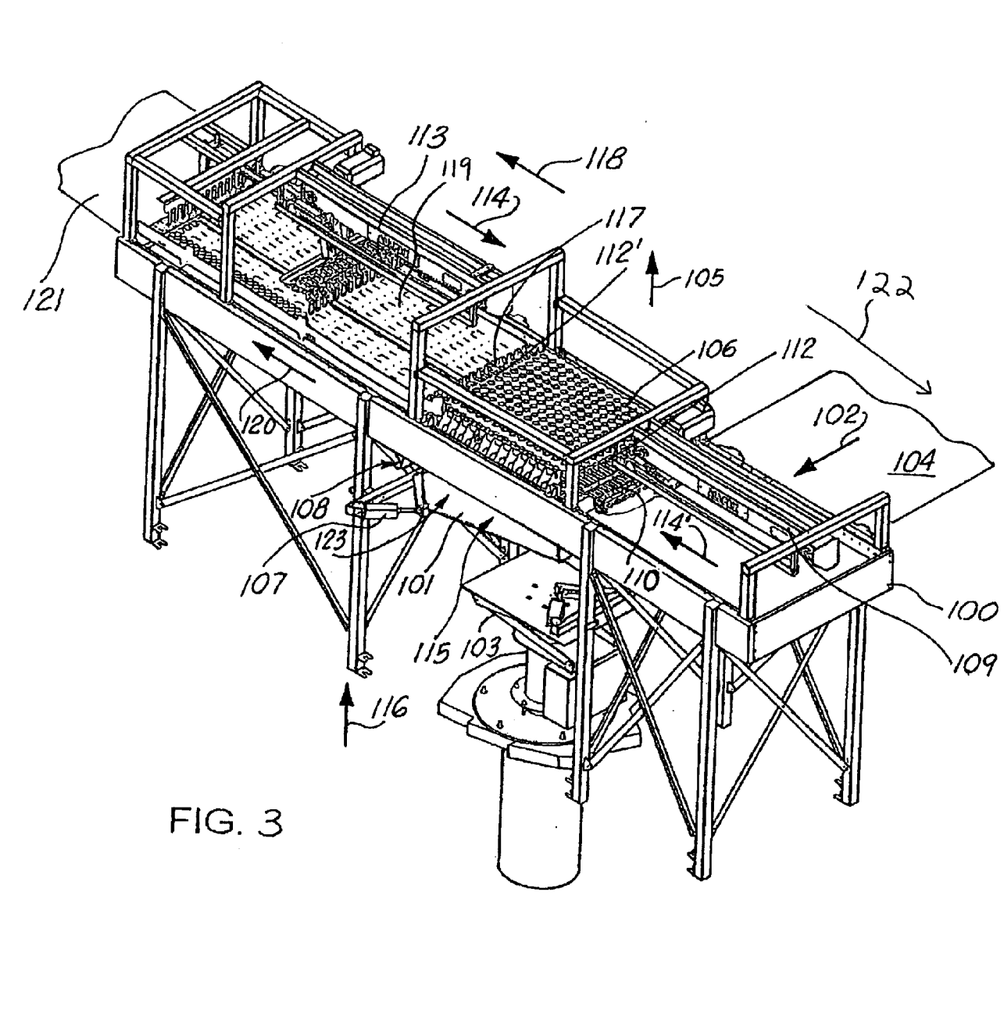
FIG. 3 is a close up, isometric view of the unloader of the preferred embodiment of the present invention.
Figure 4:
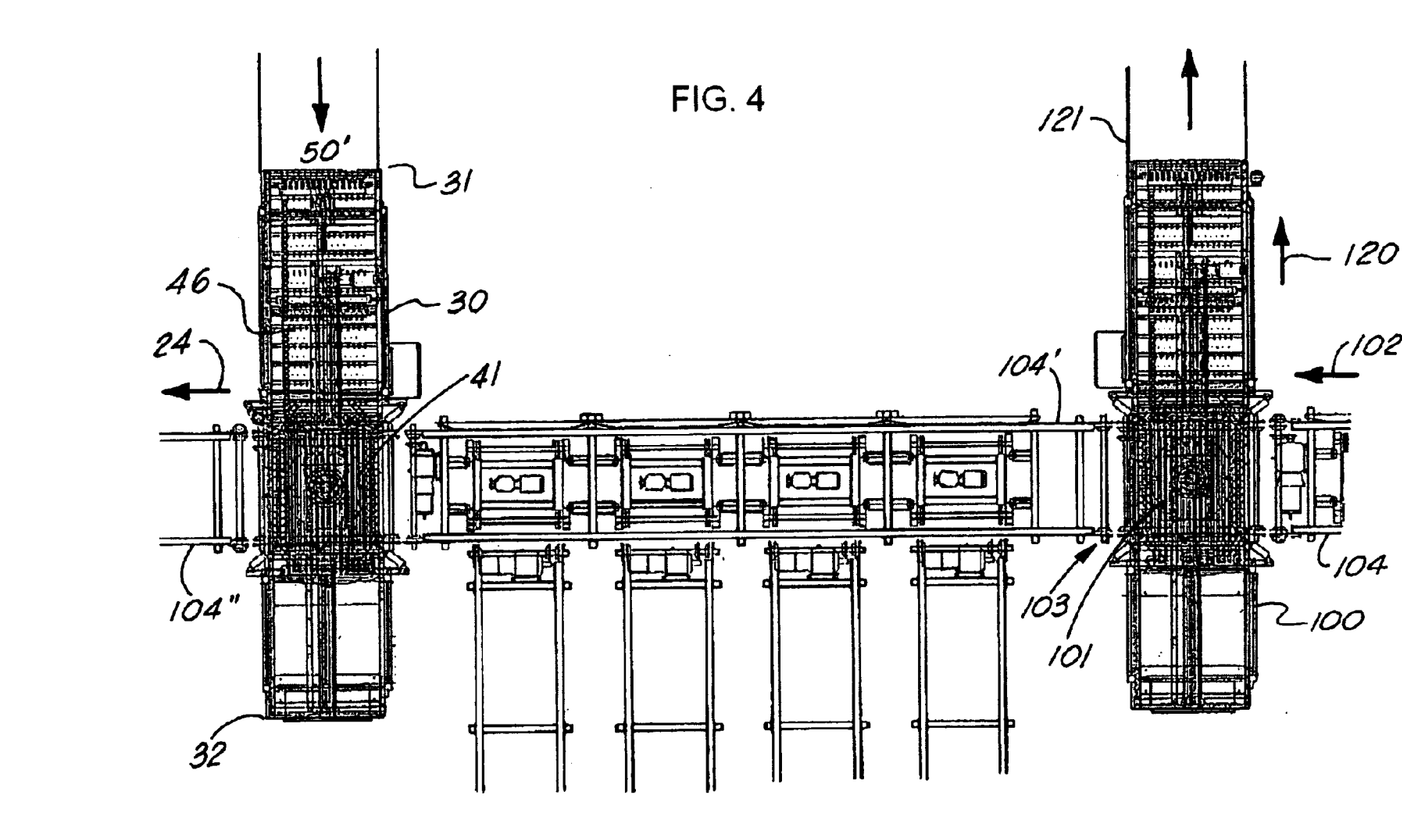
FIG. 4 is a top, partially cut-away view of an exemplary layout of the batch retort loading/unloading system of the present invention.

Continuing with FIGS. 3 and 4, the unloader 100 module operates in the same way as the loader module, but in reverse, and includes the same features and functional operation of the various elements, except it does not require the brake system of the loader module, and the follower of the loader module functions as and a pusher in the unloader module, as it is now used to urge processed product from each compartment in the tray being unloaded, and the pusher of the loader now becomes the follower in the unloader, as it is used to maintain the line of product being unloaded in an upright state.

A batch cube 101 in a basket frame forming a batch-processing basket 115 is conveyed 102 to a lift 103 at the unloader module 100 by means of a transverse exterior conveyor 104. The stack of trays or batch cube 101 is lifted 116 from basket frame and positioned at the home or unload position and indexed upward 105 to load the first tray 106. Once in position, a tray backstop 107 may be engaged and the tray support 108 is engaged to securely position the first tray for unloading. The pusher 113 advances 114 to engage product at the opening of the compartments 112' of the tray to be unloaded, to support the product 117 therein as it is urged from the tray by the follower.

The follower arms 110 of the follower 109 are then advanced 114' through each compartment 112 of the tray 106 being unloaded, while the pusher 113 is retracted 118 as the product 117 containers are removed from the tray onto the unloader conveyor 119 where the product is conveyed 120 to an exterior conveyor 121 system (again, the follower is used as the pusher in the unloader and the pusher is used as the follower in the unloader module, as opposed to visa-versa in the case of the loader module). Once the containers are fully outside the first tray in the batch cube, the follower 109 is retracted 122 fully so that the follower arms 110 are removed from the tray, the batch cube is vertically indexed 105 one position and the second tray 123 is staged for unloading. The same procedure is repeated until the entire stack of trays is unloaded.

Once the batch cube 101 has been unloaded, the lift 103 lowers the batch cube into the basket frame and loads same upon the transverse mounted conveyor 104' where it is conveyed 124 away, perhaps to the loader module 30 for loading. The next batch-processing basket (having processed product in a stack of trays therein) to be unloaded is then indexed into position.

One may appreciate that the apparatus described is suitable for loading or unloading retort baskets, but it will be appreciated that it could also be so constructed as to be suitable for only either one of these operations as well.

Both the loader and unloader are designed for fully automatic operation and use a PC or PLC for control purposes. Both modules can therefore be used in a fully automated batch retort system (A.B.R.S.) or in a semi-automated retort system in which there is some operator involvement.

ELEMENTS of the Invention

| Element | Description |
| --- | --- |
| 1 | tray |
| 2 | first, second ends |
| 3 | first second sides |
| 4 | length, width |
| 5 | top wall, bottom wall |
| 6 | height |
| 7 | spaced vertical divider walls |
| 8 | width |
| 9 | compartments for receiving a row of product along length |
| 10 | fits in |
| 11 | basket frame |
| 12 | secured by frame 360 orientation intact |
| 13 | batch cube |
| 14 | batch processing basket (multiples tacked trays multiple rows forming array |
| 15 | trays formed of stainless with apertures for heat transfer |
| 16 | floor of bottom tray (cutaway) |
| 17 | top |
| 18 | bottom |
| 19 | lifting pressure on bottom tray |
| 20 | urges top tray from frame |
| 21 | top bar which rides upon top tray, but is used to secure |
| 22, , , | side walls |
| 23 | tray support mechanism |
| 24 | away |
| 25 | |
| 26 | |
| 27 | |
| 28 | |
| 29 | |
| 30 | loader module |
| 31 | first end |
| 32 | second end |
| 33 | upper work surface |
| 34 | legs |
| 35 | medial portion |
| 36 | opening |
| 37 | batch processing basket |
| 38 | vertically indexed |
| 39 | tray |
| 40 | hydraulic ram |
| 41 | lift mechanism |
| 42 | raised edges |
| 43 | raised |
| 44 | lowered |
| 45 | |
| 46 | loader conveyor system |
| 47 | divider wall |
| 48 | product |
| 49 | line |
| 50 | end |
| 50' | Exterior |
| 51 | first brake |
| 52 | second brake |
| 53 | conveying |
| 54 | respective mini conveyor |
| 55 | sideways |
| 56 | full layer detector |
| 57 | vertical servo |
| 58 | tray support servo |
| 59 | preliminary loading area |
| 60 | final loading area |
| 61 | conveyor line 1 |
| 62 | first end of line to be loaded |
| 63 | second end |
| 64 | dead plate |
| 65 | third brake |
| 66 | raise or lower carriage |
| 67 | |
| 68 | |
| 69 | pivot |
| 70 | pusher |
| 71 | servo |
| 72 | pusher paddles |

-continued

ELEMENTS
of the Invention

| Element | Description |
| --- | --- |
| 73 | carriage |
| 74 | track |
| 75 | urge |
| 76 | pivotally affixed |
| 77 | trip detector mechanism |
| 78 | resistance |
| 79 | trip mechanism |
| 80 | follower |
| 81 | servo |
| 82 | carriage |
| 83 | follower arms |
| 84, | first, second ends |
| 85 | engagement end |
| 86 | length |
| 87 | retracting |
| 88 | track |
| 89 | servo motor |
| 90 | clear |
| 91 | rigid pusher paddles |
| 92 | clearing assembly |
| 93 | |
| 94 | |
| 95 | |
| 96 | |
| 97 | |
| 98 | |
| 99 | |
| 100 | unloader |
| 101 | batch cube |
| 102 | conveyed |
| 103 | lift |
| 104 | conveyor |
| 105 | lifted |
| 106 | first tray |
| 107 | tray backstop |
| 108 | tray support |
| 109 | follower |
| 110 | follower arms |
| 111 | forward |
| 112 | compartment of tray |
| 113 | pusher |
| 114 | advances |
| 115 | batch processing basket |
| 116 | upward |
| 117 | product |
| 118 | retracted |
| 119 | conveyor |
| 120 | conveyed |
| 121 | exterior conveyor |
| 122 | retracted |
| 123 | second tray |
| 124 | conveyed |

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

We claim:

1. A batch processing system for moving product, comprising:
    a loader basket comprising a plurality of vertically stacked trays, each of said trays having first and second ends, a length, width, depth, and an interior formed therein, said interior having formed therein a plurality of aligned compartments for receiving product therein, each of said compartments having first and second openings at said first and second ends of said tray, respectively;
    a loading module, comprising:
        a loading deck further comprising:
            conveyor receiving means for receiving product from an exterior source;
            collating means for collating said product into multiple aligned lines of product, each of said lines of product having first and second ends;
        indexing means for selectively positioning a tray in said stack of said trays in alignment with said loading deck, so as to provide a positioned tray, said positioned tray aligned with said loading deck such that each of said compartments formed in said positioned tray is further aligned with a different line of said multiple aligned lines of product, respectively;
        pushing means for engaging said first end of each of said lines of said product, so as to urge each of said lines of product into one of said separate compartments formed in said positioned tray; and
        follower means for supporting said second end of each of said lines of said product being engaged by said pushing means, so as to maintain each of said lines of said product in a uniform orientation while said pushing means is engaging each of said lines of said product.

2. The batch processing loader of claim 1, wherein there is further provided tip detection means for detecting when a product in one of said lines of product is not oriented in upright fashion.

3. The batch processing loader of claim 2, wherein said tip detection means is associated with said pushing means.

4. The batch processing loader of claim 2, wherein said tip detection means is associated with said follower means.

5. The batch processing apparatus of claim 3, wherein there is further provided:
    an unloader module for unloading product, comprising:
        a conveyor for conveying product from said unloader module;
        indexing means for positioning a tray in said stack of said trays in alignment with said conveyor, each of said trays having multiple lines of product situated therein, each of said lines of product having first and second ends;
        unloader pushing means engaging said second end of each of said lines of said product in said tray so as to urge each of said lines out of said tray onto said conveyor; and
        unloader follower means for supporting said first end of each of said lines of said product being engaged by said pushing means so as to maintain each of said lines of said product in a uniform orientation while said pushing means is engaging each of said lines of said product.

6. The batch processing apparatus of claim 5, wherein there is further provided:
    a conveyor (104') for conveying an empty stack of trays to said loader module;
    a second conveyor (104") for conveying a stack of trays having product therein from said loader module to a processor; and
    a third conveyor (104) for conveying a stack of trays having processed product from said processor to said unloader module.

7. The batch processing apparatus of claim 1, wherein said indexing means further comprises a lift mechanism for manipulating said stack of trays from said first batch processing basket conveyor so as to vertically position one of said trays in said stack of trays in alignment with said loading deck.

8. The batch processing system of claim 7, wherein said collating means comprises multiple aligned conveyors separated by divider walls, each of said conveyors having a width sufficient to enable said product to pass through each of said conveyors single file.

9. The batch processing system of claim 8, wherein said collating means further comprises brake means for selectively interrupting the passage of product through said multiple aligned conveyors.

10. The batch processing system of claim 9, wherein said multiple aligned conveyors each have a first end, second end, and medial area therebetween, and there is further provided brake means situated at said first end of each of said multiple aligned conveyors.

11. The batch processing system of claim 10, wherein there is further provided brake means situated at said medial area of each of said multiple aligned conveyors.

12. The batch processing system of claim 11, wherein there is further provided brake means situated at said second end of each of said multiple aligned conveyors.

13. The batch processing system of claim 12, wherein said pushing means comprises a servomotor driven linear motion mechanism having a carriage having a length having pusher paddles situated along said length of said carriage such that one of said pusher paddles is situated above a separate one of said multiple aligned conveyors.

14. The batch processing system of claim 13, wherein there is further provided tip detection means for detecting when a product in one of said lines of product is not oriented in upright fashion.

15. The batch processing system of claim 14, wherein each of said pusher paddles is pivotally affixed to said carriage, wherein said pusher paddles are oriented in a pushing position by a breakaway mechanism to allow one of said pusher paddles to pivot when subjected to a predetermined amount of resistance, said tip detection means further comprising means for detecting when one of said pusher paddles pivots.

16. A batch processing system for moving product, comprising:
a loader basket comprising a plurality of vertically stacked trays, each of said trays having first and second ends, a length, width, depth, and an interior formed therein, said interior having formed therein a plurality of aligned compartments for receiving product therein, each of said compartments having first and second openings at said first and second ends of said tray, respectively;
a loading module, comprising:
a loading deck further comprising:
a receiving area formed to receive product from an exterior source so as to provide received product;
a collator formed to collate said received product into multiple aligned lines of product, each of said lines of product having first and second ends;
a lift formed to selectively position a tray in said stack of said trays in alignment with said loading deck, so as to provide a positioned tray, said positioned tray aligned with said loading deck such that each of said compartments formed in said positioned tray is further aligned with a different line of said multiple aligned lines of product, respectively;
a pusher formed to engage said first end of each of said lines of said product, so as to urge each of said lines of product into one of said separate compartments formed in said positioned tray; and
a follower formed to support said second end of each of said lines of said product being engaged by said pusher, so as to maintain each of said lines of said product in a uniform orientation while said pusher is engaging each of said lines of said product.

17. The batch processing loader of claim 16, wherein there is further provided a tip detector formed to detect when said product in one of said lines of product is not oriented in upright fashion.

18. The batch processing loader of claim 17, wherein said tip detector is associated with said pusher.

19. The batch processing loader of claim 17, wherein said tip detector is associated with said follower.

20. The batch processing apparatus of claim 17, wherein there is further provided:
an unloader module formed to unload product, comprising:
a conveyor for conveying product from said unloader module;
a unloader lift for positioning a tray in said stack of said trays in alignment with said conveyor, each of said trays having multiple lines of product situated therein, each of said lines of product having first and second ends;
a unloader pusher formed to engage said second end of each of said lines of said product in said tray so as to urge each of said lines out of said tray onto said conveyor; and
a unloader follower formed to support said first end of each of said lines of said product being engaged by said pusher, so as to maintain each of said lines of said product in a uniform orientation while said pusher is engaging said first end of each of said lines of said product.

21. The batch processing apparatus of claim 20, wherein there is further provided:
a first conveyor (104') for conveying an empty stack of trays to said loader module;
a second conveyor (104") for conveying a stack of trays having product therein from said loader module to a processor; and
a third conveyor (104) for conveying a stack of trays having processed product from said processor to said unloader module.

22. The batch processing apparatus of claim 21, wherein said lift mechanism further comprises a hydraulic ram formed to provide course positioning of said stack of trays.

23. The batch processing system of claim 22, wherein said collator comprises multiple aligned conveyors separated by divider walls, each of said conveyors having a width sufficient to enable said product to pass through each of said conveyors single file.

24. The batch processing system of claim 23, wherein said collator further comprises a brake system for selectively interrupting the passage of product through said multiple aligned conveyors.

25. The batch processing system of claim 24, wherein said multiple aligned conveyors each have a first end, second end, and medial area therebetween, and there is further provided a first brake situated at said first end of each of said multiple aligned conveyors.

26. The batch processing system of claim 25, wherein there is further provided a second brake situated at said medial area of each of said multiple aligned conveyors.

27. The batch processing system of claim 26, wherein there is further provided a third brake situated at said second end of each of said multiple aligned conveyors.

28. The batch processing system of claim 27, wherein said pusher comprises a servomotor driven, linear motion mechanism having a carriage having a length transversally situated relative to said multiple aligned conveyors, and pusher paddles situated along said length of said carriage such that one of said pusher paddles is situated above a separate one of said multiple aligned conveyors.

29. The batch processing system of claim 28, wherein there is further provided a tip detector for detecting when a product in one of said lines of product is not oriented in upright fashion.

30. The batch processing system of claim 29, wherein each of said pusher paddles is pivotally affixed to said carriage, wherein said pusher paddles are oriented in a pushing position by a breakaway mechanism, so as to allow one of said pusher paddles to pivot when subjected to a predetermined amount of resistance, said tip detector further comprises a pivot detector to detect when one of said pusher paddles pivots.

* * * * *